United States Patent
Shibata et al.

(10) Patent No.: US 6,919,044 B1
(45) Date of Patent: Jul. 19, 2005

(54) SAMPLE LOADING AND HANDLING INTERFACE TO MULTIPLE CHEMISTRY ANALYZERS

(75) Inventors: George K. Shibata, Upland, CA (US);
Paul J. Ashton, Riverside, CA (US);
Scott D. Anderson, Chino, CA (US);
Steven D. Mack, Mira Loma, CA (US);
Songtai Tu, Yorba Linda, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/335,363

(22) Filed: Jun. 17, 1999

(51) Int. Cl.[7] .............................. B32B 5/02; G01N 35/00
(52) U.S. Cl. ........................ 422/63; 422/65; 422/82.05; 436/43; 436/47; 436/48
(58) Field of Search .............................. 422/63, 65, 67, 422/82.05; 436/43, 47, 48–49, 174, 180

(56) References Cited

U.S. PATENT DOCUMENTS

| 3,985,508 | A | * | 10/1976 | Williams ...................... 422/65 |
| 4,528,159 | A | * | 7/1985 | Liston .......................... 356/244 |
| 4,844,887 | A | * | 7/1989 | Galle et al. .................. 204/403 |
| 5,350,564 | A | * | 9/1994 | Mazza et al. ................. 422/63 |

(Continued)

FOREIGN PATENT DOCUMENTS

| EP | 0 977 039 | | 2/2000 |
| JP | 6207943 A | * | 7/1994 |
| WO | WO-9205448 | * | 4/1992 |

OTHER PUBLICATIONS

Excerpt from http://www.strobotics.com/r17.htm—showing an articulated robot arm having shoulder–elbow–wrist combination with gripper assembly.*

Excerpt from http://www.encyclopedia.thefreedictionary.com—describing articulated robots as being common in the pick and place application. (p. 1).*

U.S. Appl. No. 08/746,649, filed Nov. 13, 1996, Harold Fechtner et al., "Automatic Chemistry Analyzer With Sample Cup Piercing Assembly", Beckman Coulter, Inc., (formerly Beckman Instruments, Inc.), Fullerton, CA.

Primary Examiner—Jill Warden
Assistant Examiner—LaToya Cross
(74) Attorney, Agent, or Firm—Hogan & Hartson LLP

(57) ABSTRACT

A front-end system accepts samples and selectively provides aliquots of those samples to selected clinical chemistry analyzers coupled to the front-end system. The front-end system is coupled to an assembly of one or more clinical chemistry analyzers that might, for example, provide complementary analytical tools so that the overall system of front-end system and clinical chemistry analyzers provides a predetermined broad range of clinical analytical testing. The testing protocols for samples input to the overall system can be independently determined. Any sample may undergo a test within one or more of the clinical chemistry analyzers or a series of tests within a single or more typically within plural ones of the analyzers, depending upon the testing sequence defined in for that sample. The front-end system automatically identifies samples, draws aliquots, and transports the aliquots to the one or more clinical chemistry analyzers coupled to the front-end system. Sample identification, handling and testing are preferably automated A within the overall system to provide complex testing with reduced operator involvement. Consequently, the overall system may facilitate reduced operator costs and a reduced likelihood of errors in the routing and processing of samples.

28 Claims, 7 Drawing Sheets

U.S. PATENT DOCUMENTS

| | | | |
|---|---|---|---|
| 5,362,648 A | * 11/1994 | Koreyasu et al. | 436/48 |
| 5,422,075 A | * 6/1995 | Saito et al. | 422/52 |
| 5,575,976 A | 11/1996 | Choperena et al. | |
| 5,587,129 A | * 12/1996 | Kurosaki et al. | 422/64 |
| 5,599,501 A | * 2/1997 | Carey et al. | 422/63 |
| 5,623,415 A | * 4/1997 | O'Bryan et al. | 364/478.13 |
| 5,720,377 A | * 2/1998 | Lapeus et al. | 198/346.1 |
| 5,762,872 A | * 6/1998 | Buhler et al. | 422/64 |
| 5,814,276 A | * 9/1998 | Riggs | 422/65 |
| 5,833,925 A | 11/1998 | Shu et al. | |
| 5,843,376 A | * 12/1998 | Ishihara et al. | 422/64 |
| 5,863,506 A | 1/1999 | Farren | |
| 5,882,594 A | * 3/1999 | Kawaguchi et al. | 422/64 |
| 5,885,529 A | * 3/1999 | Babson et al. | 422/65 |
| 5,942,694 A | 8/1999 | Robins et al. | |
| 5,985,214 A | * 11/1999 | Stylli et al. | 422/65 |
| 6,068,437 A | * 5/2000 | Boje et al. | 414/331.02 |
| 6,117,683 A | * 9/2000 | Kodama et al. | 436/47 |

* cited by examiner

SAMPLE LOADING AND HANDLING INTERFACE TO MULTIPLE CHEMISTRY ANALYZERS

BACKGROUND OF THE INVENTION

1. Field of the Invention

The present invention relates to systems and methods for automated chemical analysis of samples and might be applied to the sort of analytical chemistry sometimes used in screening or detecting characteristics of human blood tissue or other liquid or soluble media 2. Description of the Related Art Analysis of liquids such as human blood tissue or other liquid or soluble media is commonly desirable in a variety of clinical settings. Various tests might be performed on a liquid sample to screen for different conditions or various tests might be used to accurately screen for or identify a single condition. For example, a hospital or other clinical laboratory might wish to screen a patient's blood for a plurality of conditions such as diseases so that a number of different tests might be performed on the blood. Alternately, the clinical laboratory might utilize multiple analytic techniques to establish a particular screening result with particularly high confidence. In other cases, an array of tests might be necessary to accurately diagnose a given condition. For a high volume clinical laboratory, the multiple tests that each patient might require is multiplied by the number of the many patients that might be under examination at the same time at the laboratory. Under these circumstances, it is very useful to utilize automated analytical equipment.

Automated analytical equipment, such as automated analytical chemistry workstations, can efficiently perform clinical analysis on a large number of samples, with tests being run concurrently or within short time intervals. Efficiencies result in part because of the use of automated sample identification and tracking. This equipment can automatically prepare appropriate volume samples and can automatically set the test conditions needed to perform the scheduled tests. Test conditions can be independently established and tracked for different testing protocols simultaneously in progress within a single test station, facilitating the simultaneous execution of a number of different tests based on different chemistries and requiring different reactions conditions. Automated analytical equipment is particularly well suited for high volume testing environments, such as exist in many hospitals and in centralized testing laboratories because the automatic sample handling allows for more precise sample identification and sample tracking. Automatic handling and tracking of samples significantly reduces the opportunity for human error or accidents that can lead to either of erroneous test results or undesirable contamination.

An example of such an automated clinical chemistry system is provided by U.S. Pat. No. 5,575,976 to Choperena, et al., which describes embodiments of the Access® Special Chemistry Analyzer presently available through the Clinical Chemistry Division of Beckman Coulter, Inc., located in Brea, Calif. Another automated chemistry analyzer is the SYNCHRON LX®20 General Chemistry Analyzer, as described in U.S. Pat. No. 5,863,506 to Farren, U.S. Pat. No. 5,833,925 to Hsu, et al., and in U.S. patent application Ser. No. 08/748,135 to Robins, et al., entitled "Pressure Detector for Chemical Analyzers," and in U.S. patent application Ser. No. 08/746,649 to Fechtner, et al., "Automatic Chemistry Analyzer with Sample Cup Piercing Assembly," which is also presently available through the Clinical Chemistry Division of Beckman Coulter, Inc., located in Brea, Calif. These chemistry systems can provided automated analysis of a number of samples.

There are instances when these integrated clinical chemistry analyzers are unable to perform all of the desired tests on a set of samples. For example, it may be desirable to perform tests on a given sample in both of the Access and SYNCHRON LX20 analyzers. It is desirable to run such tests in as automated of a way as possible.

SUMMARY OF THE PREFERRED EMBODIMENTS

It is an object of the present invention to provide a system for more efficiently making use of existing clinical chemistry analyzers. Alternately, preferred embodiments of the present invention may provide a more sophisticated and flexible architecture for testing samples. A consequence of implementing this architecture may be the ability to automatically perform tests including conditional testing protocols where the result of a first test either determines what subsequent tests are run, cancels subsequent tests or causes tests to be repeated.

According to an aspect of the present invention, a clinical chemistry system includes a storing station that receives and stores a plurality of primary sample tubes. A sampling station, including a sample probe that draws a volume of sample from a sample tube and transfers the volume to a secondary tube, is provided. A carriage mechanism selects one of the plurality of primary sample tubes and transports the sample tube to the sampling station and returns the primary sample tube to the storing station. A first and a second secondary tube transfer station are respectively coupled to first and second analyzers. A continuous transport mechanism moves filled secondary tubes to a selected one of the first and second secondary tube transfer stations.

Another aspect of the invention provides a clinical chemistry system with a sample identification station for determining sample identification information. A carriage mechanism transports samples to the sample identification station and a continuous transport mechanism otherwise moves sample tubes within the system. First and second sample tube transfer stations are respectively coupled to first and second analyzers. The first and second sample tube transfer stations are adapted to move a sample tube from the continuous transport mechanism to an interface of a first or second analyzer. A host computer receives sample identification information and issues a sample testing message that includes one of the first and second analyzers as a destination.

DETAILED DESCRIPTION OF THE PREFERRED EMBODIMENTS

Figure 1:
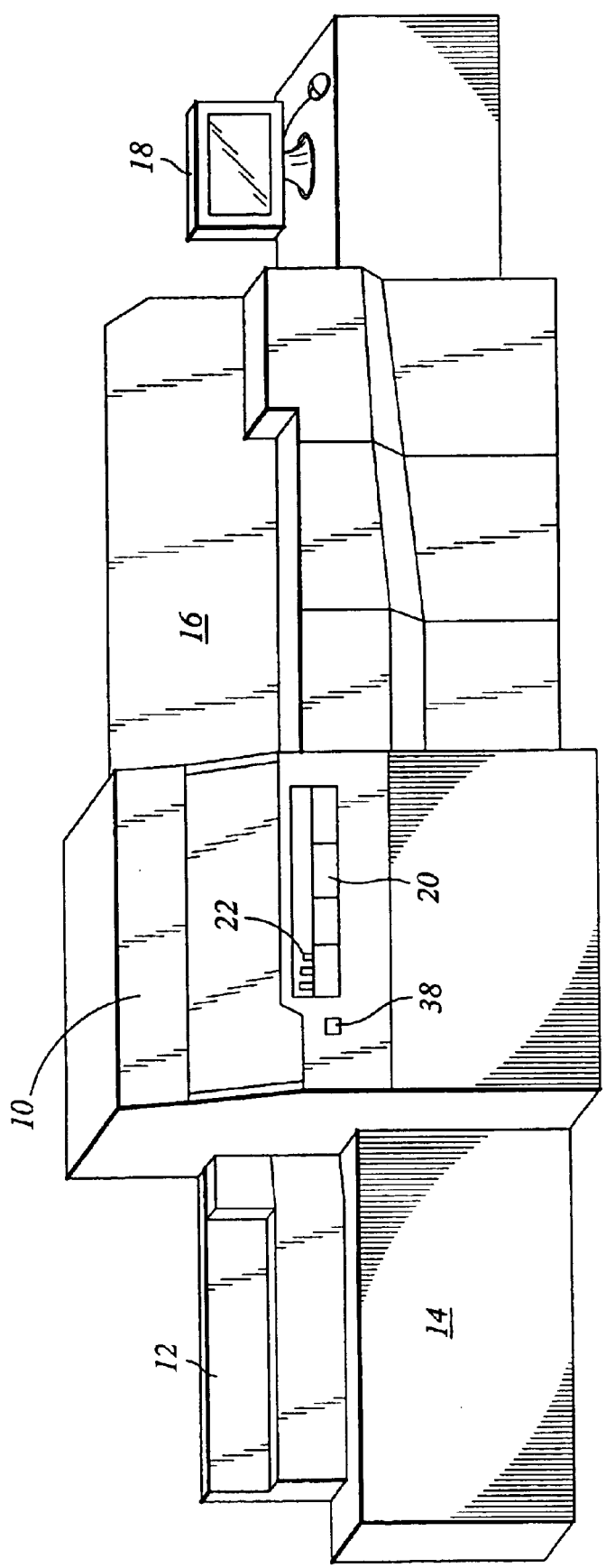
FIG. 1 provides an overview of a front-end system connected to an assembly of two different clinical chemistry analyzers.

Embodiments of the present invention provide an interface or front-end system that accepts samples and selectively provides aliquots of those samples to selected clinical chemistry analyzers coupled to the front-end system. The front-end system is coupled to an assembly of one or more clinical chemistry analyzers that might, for example, provide complementary analytical tools so that the overall system of front-end system and clinical chemistry analyzers provides a predetermined broad range of clinical analytical testing. The testing protocols for samples input to the overall system can be independently determined. Any sample may undergo a single test within one of the clinical chemistry analyzers or a series of tests within a single or, more typically, within plural ones of the analyzers, depending upon the testing protocol defined for that sample.

Most preferably, testing sequences are associated with each sample loaded into the system, whether through data input associated with the sample or through information derived from or retrieved on the basis of sample identification information attached to the sample. For example, the sample may be in a tube and information may be attached to the sample in the form of a bar code or other coded label on the sample tube. The label identifies the sample within the sample tube and might identify the tests to be performed on that sample. Alternately, the sample identification information might be used to retrieve a testing protocol from a host computer associated with the testing system. In such systems when samples are positively identified, the user can simply provide the samples to the front-end system. The overall system then performs the desired testing functions for a given testing protocol automatically, even if the testing protocol requires that tests be performed within different clinical chemistry analyzers and in specific orders. Due to the flexibility facilitated by various aspects of the present invention, it is further possible to perform conditional testing regimes, in which the results of a first test determine whether a subsequent test is to be performed or how a subsequent test is to be performed.

The front-end system automatically identifies samples, draws aliquots, and transports the aliquots to the one or more clinical chemistry analyzers coupled to the front-end system. Sample identification, handling and testing are preferably automated within the overall system to provide complex testing with reduced operator involvement. Consequently, practice of aspects of the present invention may facilitate reduced operator costs. In addition, and independently of the reduced handling aspects of the invention, practice of preferred embodiments of the present invention may provide a reduced likelihood of errors in the routing and processing of samples. This can reduce errors and reduce the need for retesting, which improves accuracy and reliability as well as reduce costs.

The front-end system preferably accepts samples in a convenient form, for example as standard-sized trays of forty or fifty standard size sample tubes or as individual sample tubes provided to one or more immediate or STAT positions. Sample tubes are automatically handled within the front-end system to extract a desired number of aliquots, generally of excess fluid volume since accurate allocations are preferably made in the destination clinical chemistry analyzers. The desired number of sample aliquots are drawn and provided to smaller tubes, referred to here as reaction vessels. These reaction vessels are individually transported to one of what may be a plurality of reaction vessel transfer stations within the front-end system. The reaction vessel transfer stations are capable of transferring the reaction vessels with their aliquots to the one or more clinical chemistry analyzers coupled to the front-end system.

When positive sample identification is provided for the input sample tubes, the front-end system automatically identifies the input sample tubes. This might be accomplished using a bar code reader and the information retrieved from the bar code label is provided to a clinical chemistry interface DataLink™ computer coupled to the front-end system and analyzers. The DataLink computer communicates what tests are to be performed on each sample and how many aliquots of the sample are required to perform those tests. Additionally, the DataLink computer determines which analyzer is to receive any given aliquot and at what times the aliquots are provided to the analyzers. It may be desirable for the front-end system to pass sample identification information directly to the clinical chemistry analyzers when such identification is useful to that analyzer. This communication provides more certain sample identification. Most of the other communication and control functions are performed by or through the DataLink computer so that the DataLink computer controls the overall system of the front-end and the clinical chemistry analyzers.

In a preferred aspect of the invention, the front-end system accesses sample tubes from the tube trays or other tube storage locations and provides the sample tubes to a sample identification station. This initial transport of the sample tubes may be accomplished by a sample tube overhead carriage and gripper capable of picking up a sample tube, transporting the sample tube with an acceptable level of accuracy and placing the sample tube at the sample tube identification station. The sample identification station may, for example, include a tube spinner positioned adjacent a bar code reader to read a bar code on the tube as the tube is spun. It should be noted that the sample tube typically only need rotate the sample tube a sufficient amount for the bar code to be read. Instead of using a tube spinner, the bar code or other identification information can be read when the overhead carriage transports the sample tube past the bar code or other reader. Most preferably, the sample identification information is then passed to the DataLink computer, which determines the testing protocol for the sample and schedules the number of aliquots to be drawn and the routing for the aliquots.

In particularly preferred embodiments of the invention, the front-end system draws aliquots from sample tubes without uncapping the sample tubes. These particularly preferred embodiments may draw aliquots from the sample tubes by piercing the sample tube caps and drawing the aliquots through the sample cap. Most preferably, the volume of sample drawn corresponds to the number of aliquots required so that the system performs a single cap piercing and a single sampling for as many aliquots of the sample as are required. The sample probe dispenses aliquots of the sample into the appropriate number of reaction vessels for that sample and that testing protocol. The reaction vessels are transported to appropriate reaction vessel transfer stations that provide the reaction vessels to the appropriate destination clinical chemistry analyzers.

In preferred embodiments of a front-end system in accordance with the invention, reaction vessels are transported within the front-end system on a continuous belt that transports the reaction vessels by the sample drawing assembly and the various reaction vessel transfer stations within the front-end system. Reaction vessels are carried on the belt within specially adapted carriages that can be accessed from the side to move reaction vessels onto and off of the carriage/belt assembly. The use of a side accessed carriage for transporting the reaction vessels allows for mechanically simpler and more precise handling of the reaction vessels, since the transport of the reaction vessels occurs primarily in a fixed horizontal plane.

Having thus provided an overview of certain embodiments of the present invention, this specification now provides a more detailed discussion of preferred embodiments of the present invention with particular reference to the drawings. FIG. 1 provides a schematic view of an embodiment of the present invention. Typical implementations of the front-end system are coupled to at least two different types of analyzers. It is, of course, possible to couple the front-end system to multiple ones of a single type of analyzer to obtain greater throughput. This is presently not considered to be a primary application of the present invention, even though aspects of the present invention facilitate such an application.

A particularly preferred embodiment of the present invention can provide a front-end system to a combination of the Access Special Chemistry Analyzer Mere, the Access analyzer) and to a SYNCHRON LX20 General Chemistry Analyzer (here, the SYNCHRON LX20 analyzer), both of which analyzers are available from the Clinical Chemistry Division of Beckman Coulter, Inc. of Brea, Calif. FIG. 1 illustrates this particular implementation. The front-end system is indicated generally at 10, the Access analyzer 12 is shown on an appropriate bench 14 and the SYNCHRON LX20 analyzer 16 is on the other side of the front-end system 10. A DataLink computer 18 controls the overall system and the testing of samples. A description of the exemplary Access Special Chemistry Analyzer can be found in U.S. Pat. No. 5,575,976 to Choperena, et al., which patent is hereby incorporated by reference in its entirety. Descriptions of aspects of the SYNCHRON LX20 General Chemistry Analyzer are provided in U.S. Pat. No. 5,863,506 to Farren, U.S. Pat. No. 5,833,925 to Hsu, et al., and in U.S. patent application Ser. No. 08/748,135 to Robins, et al., entitled "Pressure Detector for Chemical Analyzers," and in U.S. patent application Ser. No. 08/746,649 to Fechtner, et al., "Automatic Chemistry Analyzer with Sample Cup Piercing Assembly", which patents and applications are hereby incorporated by reference in their entirety. While other combinations of analyzers might be utilized, this exemplary combination of analyzers provides a practical example of an environment in which aspects of the present invention find particularly favorable application.

Figure 2:
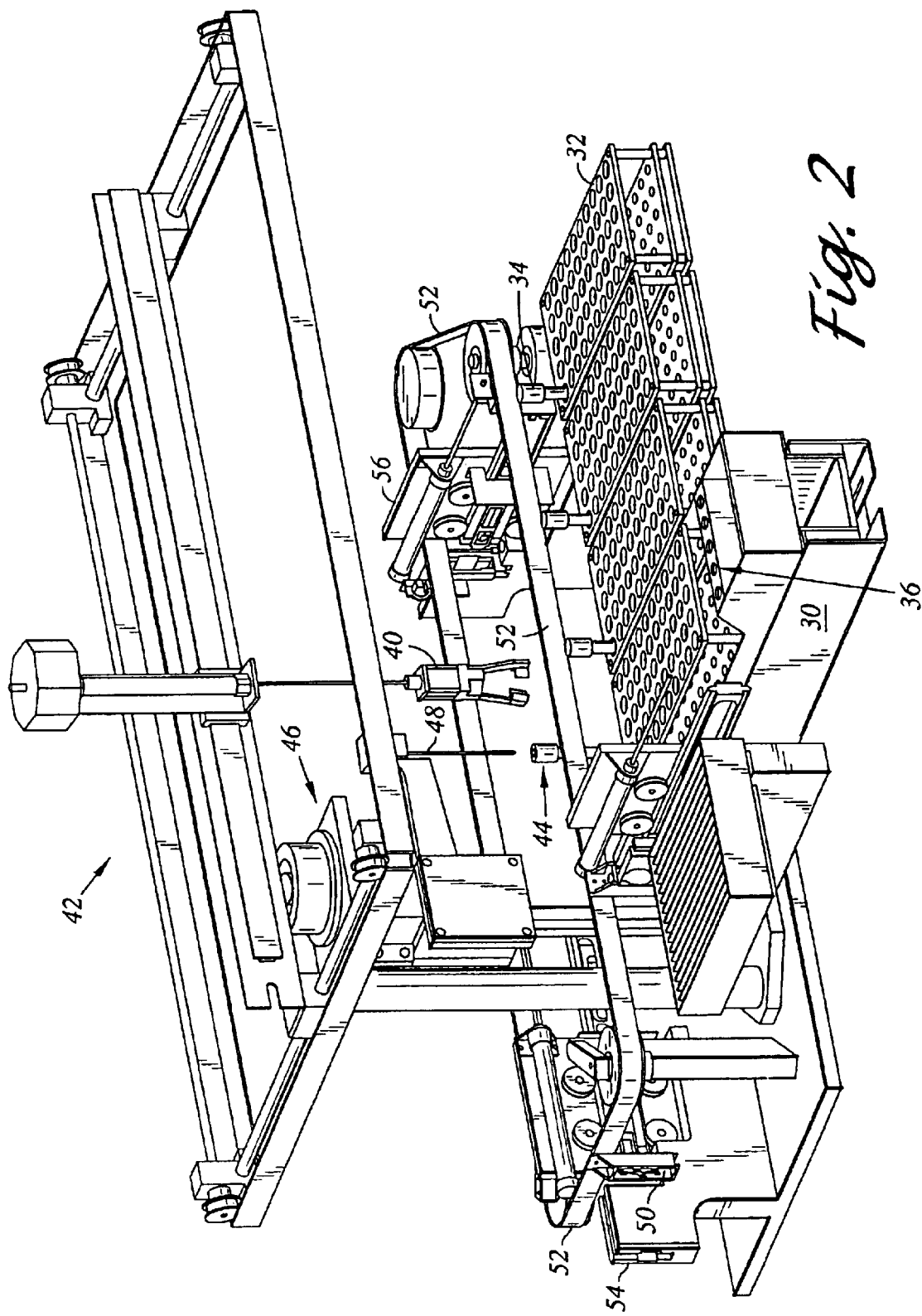
FIG. 2 provides a detailed overall view of the interior of the front-end system shown in FIG. 1.

FIG. 2 provides a partial perspective view of the transport mechanisms of the front-end system of FIG. 1. FIG. 1 shows schematically that the front-end system 10 includes a set of four drawers 20 that can be loaded with trays of sample tubes 22. One of the drawer assemblies is indicated at 30 in FIG. 2. Drawer assembly 30 extends outward from the front-end system so that an operator can load a tray 32 of sample tubes 34 into the drawer assembly 30. FIG. 2 shows all four of the sample tube trays 32 along with a few of the many possible sample tubes 34 that can be provided to the front-end system. Most preferably, the tubes provided to the front-end system are of a standard size, such as 13 or 16 millimeters in diameter and 65, 75, 93 or 100 millimeters in height. Because of the way in which the tubes are accessed, the front-end system can accept and access trays with a random assortment of different size and type tubes. In addition, because of the particularly preferred sample tube identification method, the bar codes of the sample tubes need not be aligned in any particular fashion within the trays.

Generally the samples provided to the front-end system are blood that has been centrifuged. Samples are generally cooled throughout transport and processing to preserve the samples. Most preferably, the sample tubes are maintained closed throughout processing.

Drawer assembly 30 includes a predetermined number of immediate or STAT tube locations 36. Sample tubes can be loaded into the STAT locations 36 for more immediate testing, bypassing what may be as many as two hundred samples queued in the system. Typically, an operator will load one or more sample tubes into the STAT positions and press the STAT button 38 (FIG. 1) on the front-end system. The sample handling system then accesses a sample tube from the first occupied STAT sample tube position. Aliquots are drawn from the sample tube and then the sample tube is returned to the STAT location or another output tube location. The front-end system then accesses the sample tube in the next occupied STAT tube location, until all of the sample tubes in the STAT tube locations are accessed. The system can then return to the normal processing of sample tubes.

Whether in accessing sample tubes from the STAT locations or from the many other sample tube locations within the illustrated four trays 32, sample tubes 34 are accessed using the gripper 40 of an overhead carriage assembly 42. The gripper 40 includes opposing arms that can be brought together to grip and lift successive sample tubes from the trays 32. Sample tubes are successively picked up from the sample trays 32 and transported to the sample tube identification station. FIG. 2 shows a primary sample tube 44 positioned in the sample tube identification station. Identification information is first read off of the tubes, preferably using a tube spinner and an associated bar code reader, and then aliquots are drawn from the sample tubes in accordance with the testing protocol associated with the sample identification information. After the desired number of aliquots are drawn and provided to respective ones of the reaction vessels, the sample tube is returned to the tray and a next sample tube can be accessed.

A cap piercing and sampling assembly 46 is associated with the sample tube spinner and located centrally within the apparatus of FIG. 2. Needle 48 of the assembly 46 pierces the cap of the tube positioned in the tube spinner and draws a volume of liquid from the sample tube 44. Aliquots of the sample are provided to individual reaction vessels for transport through the rest of the front-end system and eventually to the associated clinical chemistry analyzers. The needle is automatically cleaned between samplings to ensure sample integrity.

Reaction vessels are transported throughout the front-end system in carriages 50 specially adapted for securely holding the reaction vessels and allowing access to the reaction vessels from the sides. Side access is useful for ease in transferring and transporting the samples through the system. The reaction vessel carriages are mounted on a continuous belt that travels around the periphery of the front-end system. The carriages 50 and belt 52 eventually transport the reaction vessels to one of at least one and preferably two or more reaction vessel transfer stations 54, 56. These reaction vessel transfer stations 54, 56 move the reaction vessels from the belt to a transport mechanism adapted for delivering the reaction vessels into the target associated clinical chemistry analyzer. Considering the assembly illustrated in FIG. 2 within the overall system illustrated in FIG. 1, transfer station 54 might be associated with the Access analyzer 12 and transfer station 56 might be associated with the SYNCHRON LX20 analyzer 16.

Individual components of the system illustrated in FIG. 2 are now described further with reference to a number of sub-assembly drawings.

Figure 3:
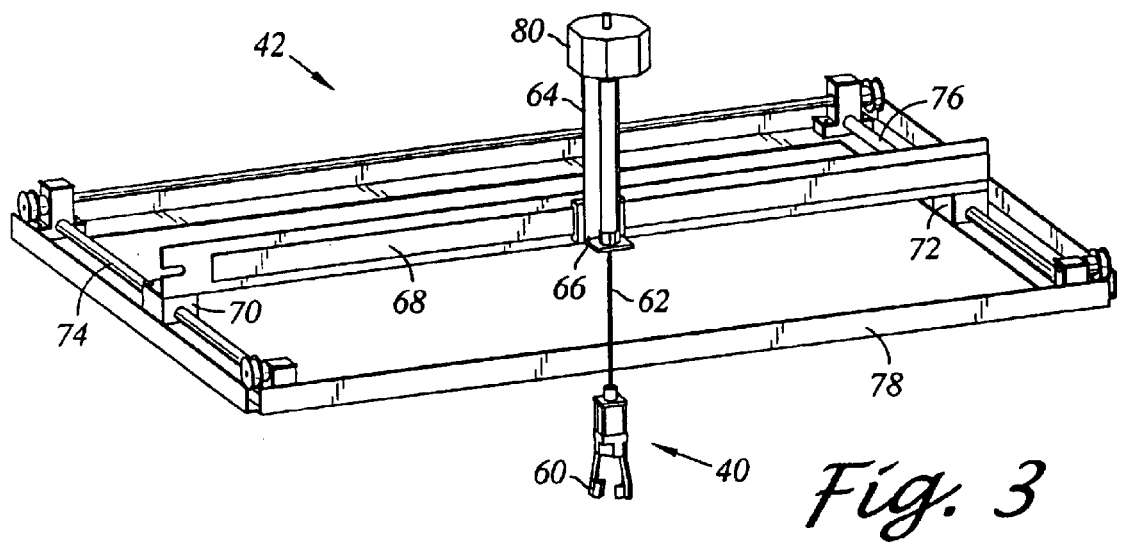
FIG. 3 illustrates more clearly the overhead carriage and gripper assembly of FIG. 2.

FIG. 3 shows a further view of the overhead carriage and gripper assembly 42 of FIG. 2. Tube gripper 40 includes a pair of opposed arms 60 that can be closed on a sample tube to grip the tube. Preferably the arms are of a sufficient length so that the gripper 40 grips a sample tube just above the tray as the tube sits upright in the tray. This allows the sample tubes to more readily be of arbitrary length while still ensuring the sure grip of the sample tube by the gripper. The arms 60 of the gripped preferably operate under pneumatic control, with pneumatic communication to the arms effected through a portion of sleeve 62 that extends between the carriage and the gripper. In other instances, another mechanism might be used for opening and closing the arms. Sleeve 62 moves within air piston 64 to move the gripper either up or down, as required to transport the sample tube safely away from the tray and to the tube spinner.

The air piston 64 and gripper assembly are mounted to the carriage frame by a slide bracket 66 mounted on a linear ball slide 68. The slide bracket moves the gripper assembly along the direction of the X-axis as required for positioning the sample tube held by the gripper 40. The linear ball slide 68 is mounted on either end to pillow bearings 70, 72, which are in turn slidably mounted to rods 74, 76 extending in the Y-axis direction to facilitate translation of the gripper assembly along the direction of the Y-axis. The carriage includes a generally rectangular frame 78 that holds the various components in fixed relation with one another. Not illustrated in the figure are the various belts and translation motors, generally known in the art, that are used in translating the gripper assembly to its desired position. Actuation of the various illustrated elements and the process of positioning sample tubes within the front-end system is controlled by a controller within the front-end system, also not shown in FIG. 3.

Air piston 64 and the gripper assembly may be provided with a motor 80 capable of spinning a tube held in the gripper. This optional additional motor might be used if, instead of providing a tube spinner within the front-end system, the gripper is used to spin a sample tube. In this alternative embodiment, the overhead carriage and gripper assembly positions a sample tube adjacent a bar code reader. The gripper assembly then rotates the tube sufficiently, in this case through approximately 270°, to facilitate reading the bar code information from the label on the sample tube. Other variations on the particular components illustrated in FIG. 3 are, of course possible, so long as the primary purpose of safely and accurately transporting sample tubes in three dimensions is met.

Figures 4, 5:
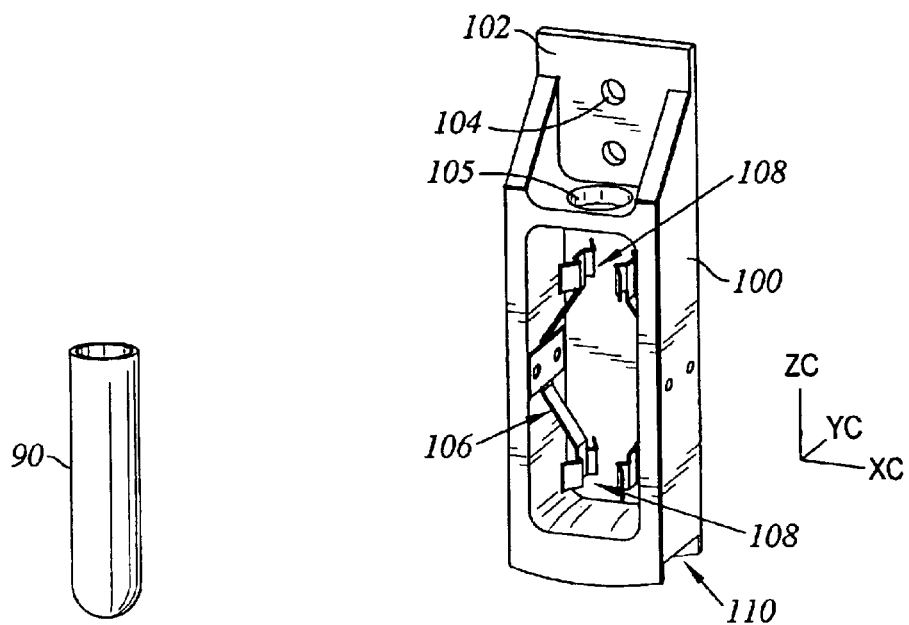
FIG. 4 shows a reaction vessel for carrying an aliquot of a sample within the overall system.
FIG. 5 shows a carriage with clips for holding a reaction vessel in place within the carriage.

Aliquots of samples are dispensed into reaction vessels and transported through the front-end system within reaction vessels, such as the one indicated at 90 in FIG. 4. Reaction vessels 90 can be of various sizes and shapes, but will preferably contain an amount of liquid on the order of the largest aliquot that will be required by the associated clinical chemistry analyzers. In the illustrated embodiment, the reaction vessels are preferably substantially clear plastic tubes that can readily be rendered clean and sterile, whether as a result of manufacture or through subsequent cleaning.

FIG. 5 shows a carriage 100 specially adapted for carrying a reaction vessel such as reaction vessel 90 shown in FIG. 4. In a preferred embodiment, the carriage 100 is formed from a material whose dimensions do not vary appreciably over an effective temperature range, is sturdy and durable, and is easily formed. The carriage might, for example, be plastic. The carriage 100 is provided with a vertically extending flat portion 102 that is suited for mounting the carriage onto a carrier of some type, for example a belt in particularly preferred embodiments of the present invention. Connector holes 104 are provided for attaching the carriage to the carrier. An access hole 105 is provided through which the volume of the reaction vessel can be accessed. In particularly preferred embodiments of the present invention, a sample probe can be extended through the access hole 105 to allow an aliquot to be delivered into the reaction vessel.

Preferably the carriage 100 is open on at least two sides to allow for laterally moving reaction vessels onto and off of the carriage 100. Clips 106 are provided on opposite sidewalls of the carriage and are positioned so that holding faces 108 of the clips are spaced apart by an amount less than the diameter of a reaction vessel. The clips 106 are preferably formed from a resilient structure, which could be metal but is more preferably plastic and molded with the rest of the carriage to facilitate volume manufacture of the carriage. Opposing faces 108 of the clips 106 positioned on opposite walls of the carriage effectively provide cups or stable positions for holding the top and bottom of a reaction vessel. Most preferably the arms of the clips 106 are sufficiently springy to firmly grip reaction vessels, while still allowing a reaction vessel to be moved onto and off of the carriage 100 without excessive force and without too violent of motions.

Movement of reaction vessels onto and off of the carriage is, in particularly preferred embodiments of the invention, further facilitated by downwardly extending legs 110 that mate with receiving grooves at reaction vessel transfer stations to hold the carriage in a position laterally fixed in the direction opposite to the force applied to the carriage. The illustrated embodiment of a carriage includes front and back legs for holding the carriage in place during transfer of a reaction vessel. It should be appreciated that other configurations of extensions can be provided that can slide into a corresponding receiving structure to hold the carriage in position during transfer. The carriage need not be precisely held in place. Rather, the preference for holding the carriage in place during transfer of the reaction vessel is that movement of reaction vessels in adjacent carriages be sufficiently small as to not present a significant danger of spilling or splashing liquid from the adjacent reaction vessels.

Figure 6:
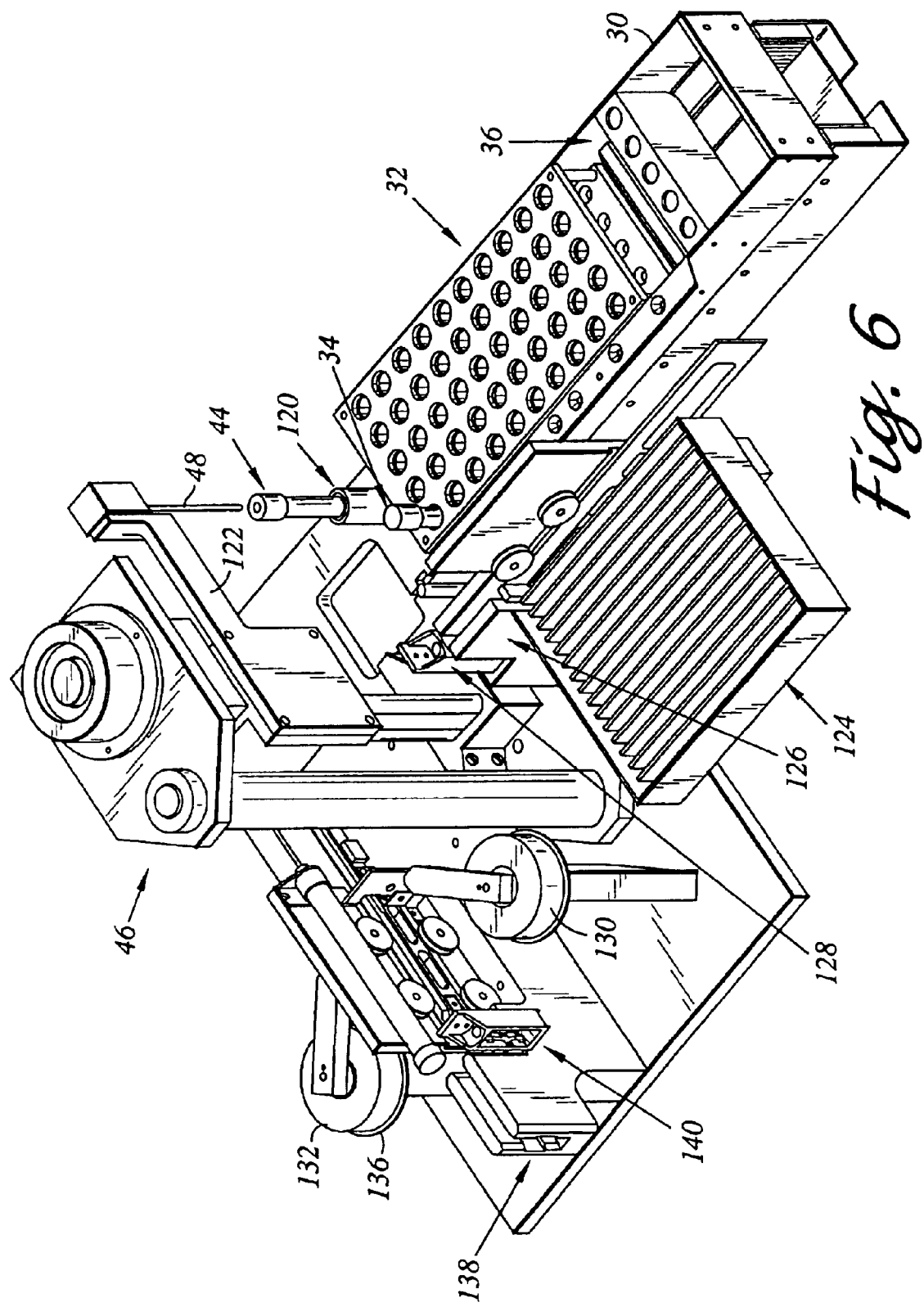
FIG. 6 shows a clearer view of the cap piercing and sampling assembly in relation to other components of the overall system.

FIG. 6 more clearly illustrates the cap piercing and sampling assembly 46 in relation to other components of the system. The overhead carriage 42 and the belt 52 are not shown in the sub-assembly view of FIG. 6. Drawer assembly 30, like that illustrated and discussed with reference to FIG. 2 above, carries a sample tray 32 with a sample tube 34 within a rack 32. The overhead carriage and gripper transports a sample tube to the tube spinner 120, which holds the tube 44 so as to expose the bar code or other identification label provided on the sample tube. Preferably, the tube spinner centrally positions and securely holds tubes of different diameters both so that the tubes can be spun and so that the tubes are accurately located for drawing aliquots of the sample. This can be accomplished better using a tube hold down assembly, discussed below with reference to FIGS. 8 and 9. After the initial transport, the sample tube is spun so that a bar code reader can read the bar code information from the sample tube. Responsive to the sample identification information, a host computer determines what tests are to be run on the sample and issues a request to the front-end system for a number of aliquots to be drawn and passed on to the clinical chemical analyzers.

Sample tube 44 is held securely in the tube spinner 120 so that the cap on the sample tube can be pierced. The cap piercing and sampling assembly 46 provides a sample probe having a non-coring needle 48 for piercing the cap of the sample tube. The needle 48 is mounted on an arm 122 that is vertically translated so as to extend through the cap of the sample tube 44. The sampling assembly provides liquid level sensing for the needle 48 so that the needle is accurately positioned with respect to the liquid within the tube, allowing either different size tubes or different sample volumes to be used within the testing system.

When the needle is properly situated within the sample liquid, the desired volume of liquid equal to the number of desired aliquots times the volume of each aliquot desired is drawn from the sample tube. The appropriate volume of sample is drawn from the sample tube using a controlled pressure and vacuum mechanism operatively connected to the needle of the sampling assembly. As the sample is drawn into the needle, the system tests for the presence of clots, for example by monitoring the pressure present at the needle. If a clot is found as the sample is drawn, positive pressure is applied to clear the needle and the aspiration of the sample will begin again. Most preferably, an optical probe is provided in communication with the sample drawn through the needle and probe that is capable of performing a variety of optical measurements on the sample as it is drawn.

After drawing the sample, the arm 122 is translated vertically again to remove the needle 48 from the sample tube 44. Although not shown here, it is often useful to provide an auxiliary arm to hold the cap on the top of the sample tube so that the cap remains in place as the needle is withdrawn from the sample tube. The drawn sample volume is held within the sampling assembly. The sampling arm 122 and the needle 48 are rotated so that the needle is positioned over the first reaction vessel to be filled. Positive pressure is applied and the desired aliquot of sample is output into a reaction vessel. The dispensed reaction vessel is translated away from the filling positioned and a new reaction vessel is positioned and then filled to the desired level. This process continues until the desired aliquots have been dispensed.

The needle and sampling assembly are then cleaned to prepare the assembly for further sampling. The accessed sample tubes are moved by the carriage and gripper assembly to an output position within the previously accessed tray or into a tray used as an outgoing tray. This description of the cap piercing and sampling assembly is abbreviated. Further description and an alternate embodiment of a cap piercing assembly can be found in the previously incorporated by reference U.S. patent application Ser. No. 08/746,649 to Fechtner, et al., entitled "Automatic Chemistry Analyzer with Sample Cup Piercing Assembly." application Ser. No. 08/746,649 is hereby again incorporated by reference in its entirety for its teachings regarding the design and operation of a cap piercing and sampling assembly, including a cleaning station for the sample probe.

Referring still to FIG. 6, empty reaction vessels are stored in a bin 124 and are removed from the bin by a reaction vessel feeder 126. The reaction vessel feeder moves individual reaction vessels from the bin onto a carriage 128 positioned for receiving a reaction vessel from the bin.

Sample aliquots are dispensed into reaction vessels from the needle 48 of the sample probe according to the testing protocols associated with the identification information associated with the sample. The position of the reaction vessel for the liquid transfer operation may be within the holding bin 124 or the reaction vessel may be within the carriage 128 through an opening provided on an upper surface of the carriage.

Carriages with filled reaction vessels are moved away from the reaction vessel transfer feeder 124 by translation of the belt 52 (FIG. 2) along with the attached carriages 128 (FIG. 6). Although it is not illustrated here, the belt typically has connected to it many of the carriages 128 positioned in close relationship to each other. The belt may be translated in either direction to move each reaction vessel to its destination clinical chemistry analyzer. In practice, however, the belt translates an assembly of carriages carrying filled reaction vessels in the same clockwise or counterclockwise direction. The belt 52 is held at a desired vertical position by wheels positioned along the periphery of the front-end assembly. Four such wheels are shown in FIG. 2; two of these wheels 130, 132 are shown in greater detail in FIG. 6 and include lips 136 to support the belt and hold the belt in a substantially fixed and constant vertical position. Preferably the belt is formed from a durable material having good flexibility in the direction of its thinner dimension, with a substantial degree of support along the vertical in the installation of the belt 52 illustrated in FIG. 2. Lateral motion of the belt is limited somewhat in practical operations by tension applied to the belt.

The belt translates filled reaction vessels around the periphery of the assembly of the front-end system, moving the reaction vessels from the vessel feeding station 126 to one or more reaction vessel transfer station. The reaction vessel transfer stations move the reaction vessels from the front-end system into a mechanical interface associated with the target clinical chemistry analyzer. One such reaction vessel transfer station is indicated at 138 in FIG. 6. A carriage about to be received by the reaction vessel transfer station 138 is indicated at 140.

Figure 7:
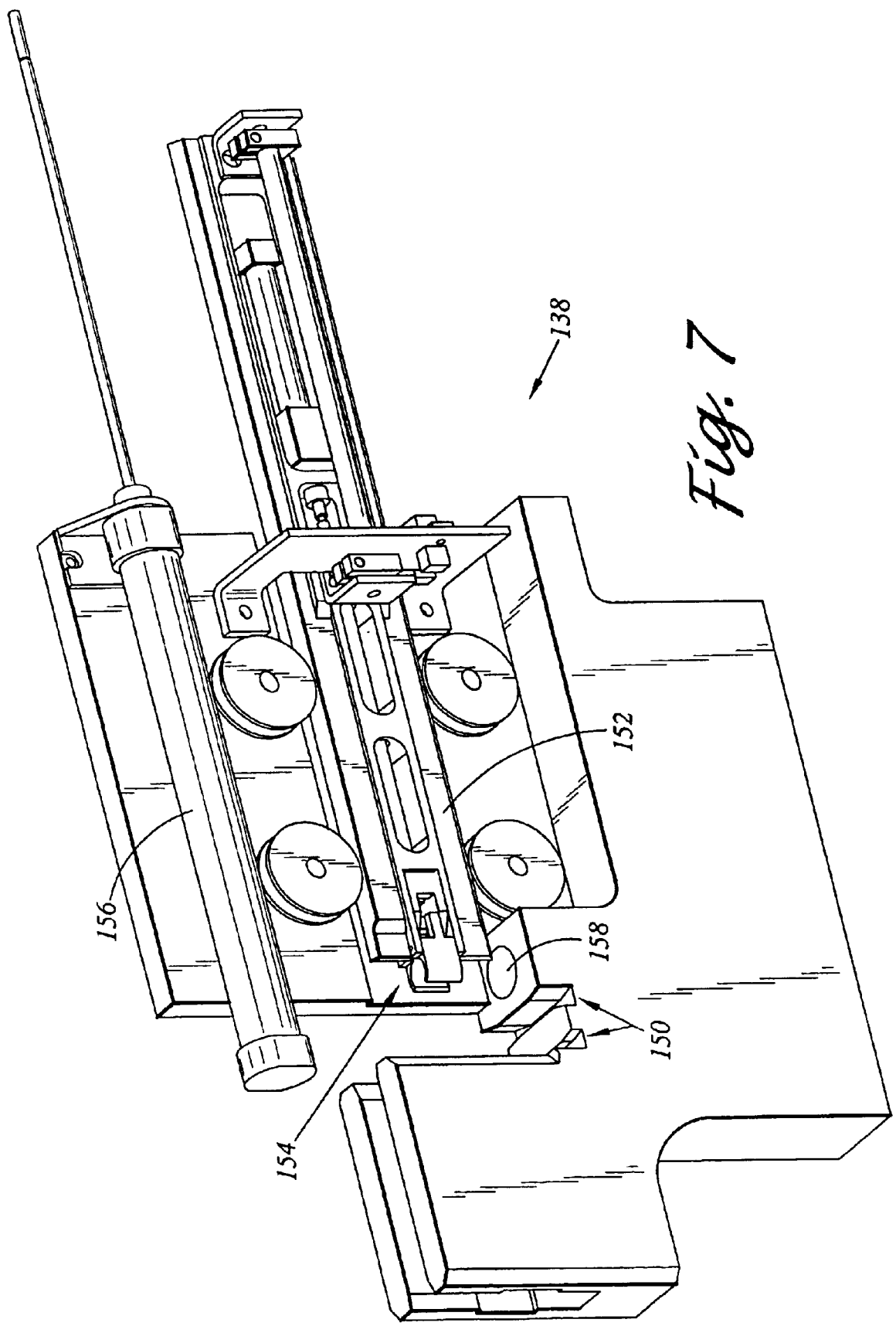
FIG. 7 illustrates a reaction vessel transfer mechanism.

The reaction vessel feeder 126 of FIG. 6 and the reaction vessel transfer station 138 are better illustrated in FIG. 7. A carriage is translated on the belt, neither illustrated in this view, to place the carriage in position to transfer the reaction vessel onto or off of the carriage. The feeder or transfer station includes a set of grooves 150 for receiving the legs 110 (FIG. 5) of the carriage. Grooves 150 are tapered to be wider at the entrance and exit to the grooves and narrower at a central portion that holds the carriage in place during a transfer operation. The tapering of the grooves makes it easier for carriages on the belt to be guided into the reaction vessel transfer position, thereby reducing the tolerances required in translating the carriages on the belt. When the carriage is in proper position, a transfer arm 152 extends to move the reaction vessel onto or off of the carriage.

Grippable fingers 154 are provided on the transfer arm 152 to hold a reaction vessel during a transfer operation. When the apparatus of FIG. 7 is used as a reaction vessel feeder, reaction vessels are fed laterally to a position approximately at the illustrated position of the fingers. The fingers 154 grip the fed reaction vessel and the arm 152 extends to insert the reaction vessel into the carriage 100 so that the reaction vessel 90 is securely held within the clips 106 of the carriage. Movement of the transfer arm may be accomplished by an air cylinder 156 under the control of the controller for the front-end system. Similarly, the gripping motion of the fingers 154 is accomplished by conventional mechanisms under control of the controller for the front-end system.

When the apparatus of FIG. 7 is used as a reaction vessel transfer station, a filled reaction vessel is within the carriage initially presented to the transfer station. The transfer arm extends out, accessing the carriage from the side and gripping the reaction vessel within the carriage. After the fingers 154 firmly grip the reaction vessel, the transfer arm 152 is extended further to provide the reaction vessel to the receiving portion of the associated clinical chemistry analyzer. In practice, the transfer arm is preferably of sufficient length to deliver the reaction vessel into the sample wheel of a closely situated Access analyzer or into a similar receiving assembly in the SYNCHRON LX20. Preferably, after reaction vessels are used in the target clinical chemistry analyzer the transfer arm retrieves the reaction vessel from the clinical chemistry analyzer for disposal. As illustrated in FIG. 7, the reaction vessel transfer station (but not the reaction vessel feeder) is provided with a hole 158 through which used reaction vessels can be dropped. When used reaction vessels are retrieved by the front-end system from the clinical chemistry analyzer, the reaction vessels are provided through the hole 158 directly to a prepared biohazard receptacle.

Figure 8:
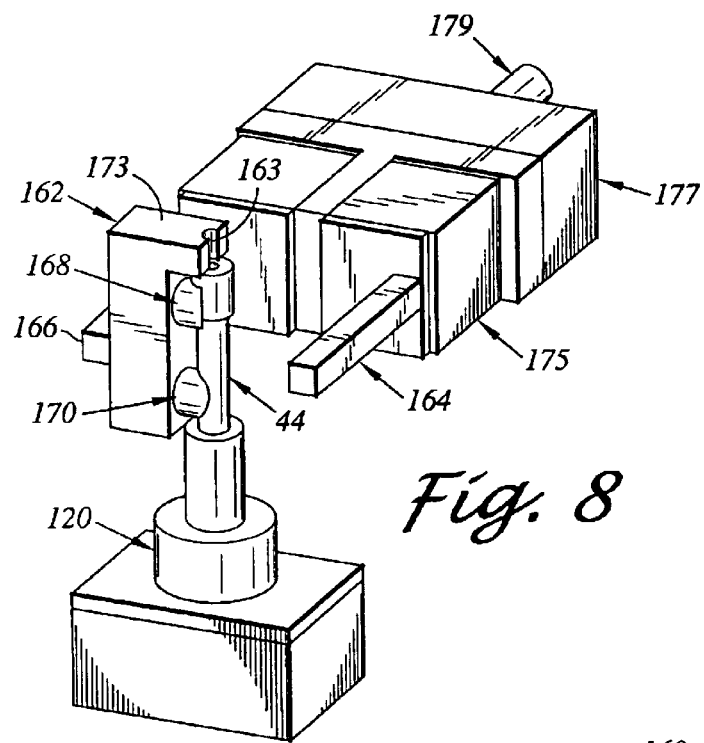
FIGS. 8 & 9 illustrate views of a mechanism for centering and holding a sample tube during a cap piercing operation.
Figure 9:
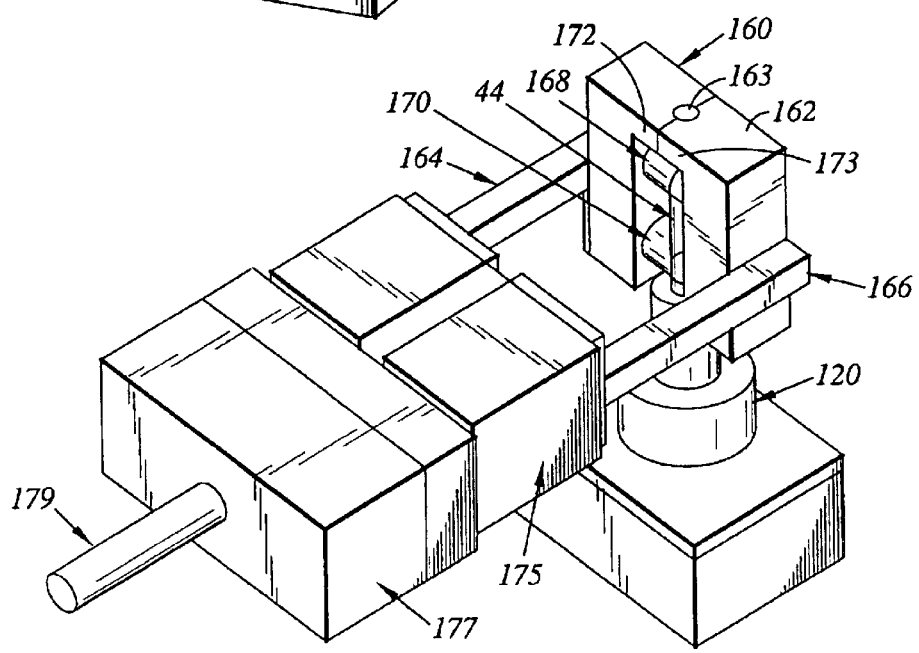

FIGS. 8 and 9 show complementary views of a preferred assembly for centering and holding sample tubes 44 in the preferred tube spinner 120 during cap piercing and sampling operations. FIG. 9 is a partially disassembled view to better illustrate the structure. The tube centering and holding assembly includes first and second opposing jaws 160, 162 that can be closed around a sample tube 44 positioned within the tube spinner 120. In the illustrated embodiment, it is unimportant whether the tube is held in a tube spinner so long as the tube is held appropriately for access by a sample probe. When jaws 160, 162 are closed around the sample tube 44, an opening 163 is provided between the jaws 160, 162 to allow the sample probe needle (48 in FIG. 6) access to the capped sample tube 44. The jaws 160, 162 are opened and closed by movement of the actuator arms 164, 166 on which the jaws are respectively mounted.

First and second sets of opposing buttons 168, 170 are provided on the opposing faces of the jaws 160, 162. The buttons 168, 170 are retractable and have cupped faces so that, when the jaws 160, 162 close around a sample tube 44, the buttons retract within their respective jaws and center the sample tube with respect to the opening 163 between the jaws. Typically the buttons are spring-loaded so that, when no tube is present between the buttons, the sample buttons extend from the faces of the jaws. In practice, the lower set of buttons 170 is sufficient to center all sizes of tubes; for shorter tubes the top set of buttons 168 will not be used for centering. For shorter tubes, the upper set of buttons close above the tube, leaving an opening between the button faces through which the sample probe needle can extend. The upper buttons 168 also serve to hold down the lower tube when the sample probe needle is withdrawn from the sample tube cap. For taller tubes, the laterally extending arms 172, 173 of the jaws serve as the hold down mechanism for withdrawing the probe needle from the taller capped sample tube. As illustrated in FIG. 9, the jaws and extending jaws are preferably sized to allow the arms 172, 173 to be positioned adjacent the top of a capped tall (e.g., 100 mm) sample tube.

The jaws of the centering and holding assembly are laterally positioned by movement of actuator arms 164, 166, which extend from a pair of actuator elements 175 which move with respect to a fixed body 177. Movement of the actuator elements and hence the jaws 160, 162 is accomplished by air pressure and/or vacuum provided through air cylinder 179. The assembly of FIGS. 8 and 9 is positioned with respect to a sample tube in the tube spinner after the sample identification operation is complete and the jaws are closed around the sample tube to facilitate the cap piercing and sampling operations.

All of the mechanical elements shown in FIGS. 2–3 and 6–9 are operated under control of the controller for the front-end system. A conventional control system is provided to effect motor control and other conventionally known functions for effecting the automatic control and operation of the illustrated systems. Process monitors might be provided throughout the front-end system to ensure proper operation of the various positioning mechanisms. Such process monitors would provide feedback directly to the controller for the front-end system. Similarly, an overall and coordinated control system is preferably provided to the control system.

Figure 10:
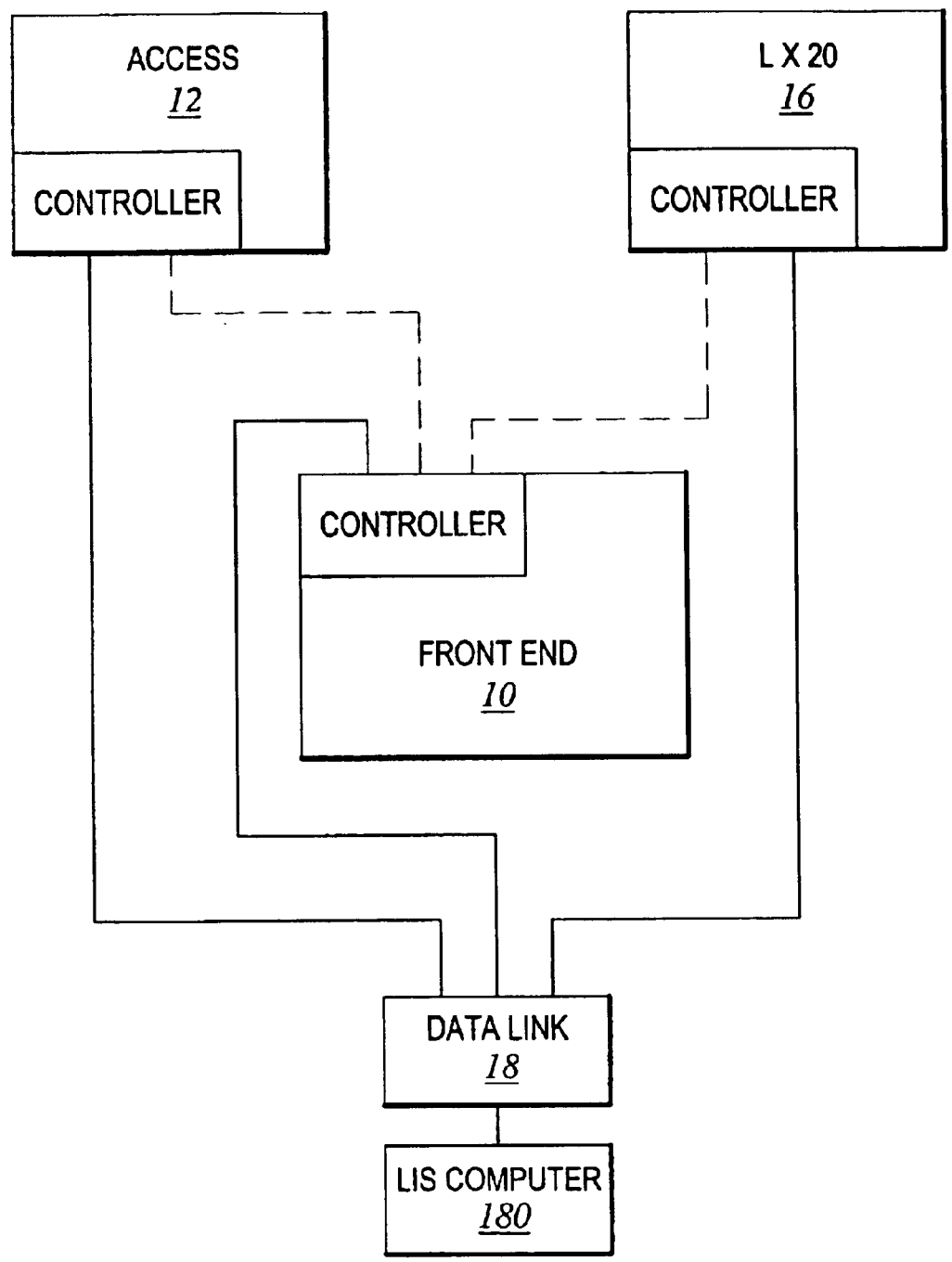
FIG. 10 schematically illustrates the interconnections of control systems and computers in the system of FIG. 1.

FIG. 10 provides an operational overview of a control system for the FIG. 1 system. In discussing the control system of FIG. 10, it is convenient to assume that all sample tubes input to the system are labeled with a bar code that identifies the samples with a unique number and that directly or indirectly defines a series of tests to be performed on the sample. Test assignments are preferably stored in or accessed by the DataLink computer 18, which may be integrated with an overall laboratory information system (LIS) computer 180 when the FIG. 1 system is provided in a hospital or clinical environment. Tests might be associated with a particular sample within the LIS computer 180 in a manner that can be accessed by the DataLink computer and provided to the front-end system 10 and the chemistry analyzers to schedule the testing protocols applied to the various samples.

The DataLink computer 18 acts as an interface between the controllers within each of the front-end system 10 and the clinical chemistry analyzers 12, 16 and, in some implementations, an LIS computer 180. A sample is input to the system and transported to an identification information reading station such as the spinner and bar code reader assembly discussed above. The bar code or other code is read and the sample identification information is transferred through the controller of the front-end system to the DataLink computer 18. The DataLink computer responds to receipt of the sample identification information by looking up the tests to be performed on that sample. In some embodiments, this look up operation is accomplished by accessing an LIS computer 180. The DataLink computer 18 transmits a schedule of test requirements for the sample, including an instruction on the number of aliquots to be drawn from the sample. If the sample identification is not stored within the DataLink computer 18, an error is flagged, the sample tube is not sampled and the tube is transported to a sample tube output position.

The front-end system 10 draws aliquots from a sample tube in accordance with instructions from the DataLink computer 18. The controller of the front-end system keeps track of the sample identification information associated with each filled reaction vessel on the belt. When a sample tube reaches the reaction vessel transfer station associated with the target clinical chemistry analyzer, the front-end system issues a message to the target clinical chemistry analyzer. The target clinical chemistry analyzer acknowledges receipt of the message and sends a return message that the target clinical chemistry analyzer is ready to receive a reaction vessel. The front-end system 10 then issues a message that identifies the sample by its identification information to the target clinical chemistry analyzer 12 or 16.

After this "handshaking" procedure is complete, the reaction vessel is transferred to the target clinical chemistry analyzer and the analyzer issues a message confirming receipt of the reaction vessel. The target clinical chemistry analyzer then issues a message to the DataLink computer requesting testing instructions for the received sample. The DataLink computer 18 provides the target clinical chemistry analyzer with testing instructions, which are associated with the sample identification information and position within the analyzer. The analyzer then proceeds through its assigned testing protocols. Independent of this testing, additional reaction vessels corresponding either to this sample or other unrelated to this sample might be transferred into one or more of the analyzers, repeating the sample transfer handshaking and protocols described above.

When chemistry tests are completed on a given reaction vessel, the results of the tests are transferred back to the DataLink computer 18. The DataLink computer can then make decisions as to whether additional tests are to be run on the sample or if tests should be repeated or if operator intervention is required. The analyzers associated with the front-end system operate independently but under central control. In this way, highly flexible testing regimes can be practiced automatically, that is, without operator intervention. Different sequences of tests within different analyzers can be programmed and sequenced in the system. For example, an initial test can be scheduled in the illustrated SYNCHRON LX20 analyzer and later a test can be run in the illustrated Access analyzer. Additionally, a decision as to whether the later Access test should be run or not can be made as a result of the earlier testing in the SYNCHRON LX20 analyzer.

By adding the described and illustrated front-end system and appropriate computer controls to an assembly of already available clinical chemistry analyzers, a significant improvement in flexibility and efficiency can be obtained. At the same time, embodiments of the present invention can facilitate a reduction in the possibility of handling or routing errors, reducing the need for retesting and reducing the possibility of reporting erroneous results.

While the present invention has been described in terms of certain preferred embodiments thereof, those of ordinary skill in the art will appreciate that variations and modifications on the described embodiments can be made within the general teachings of the present invention. Consequently, the scope of the present invention is not to be limited to any particular embodiment described herein but is instead to be determined from the claims, which follow.

What is claimed:

1. A clinical chemistry system comprising:
    a storing station that receives and stores a plurality of primary sample tubes;
    a sampling station including a sample probe that draws a volume of sample from a primary sample tube and transfers the volume to a secondary tube;
    a carriage mechanism, comprising a gripper with a pair of opposed arms that close on one of the plurality of primary sample tubes, grips it, lifts it, and transports the primary sample tube from the storing station to the sampling station and returns the primary sample tube from the sampling station to the storing station;
    a first and a second secondary tube transfer station, respectively, for coupling to first and second anal analyzers, the first and second sample tube transfer stations adapted to move the secondary sample tube from a continuous transport mechanism to be received by a corresponding one of the first and second analyzers; and
    the continuous transport mechanism for moving filled secondary tubes to a selected one of the first and second secondary tube transfer stations;
    wherein the continuous transport mechanism is a continuous belt that travels adjacent the sampling station and the first and second secondary tube transfer stations;
    wherein a plurality of sample tube carriages are mounted to the belt, each sample tube carriage adapted for carrying the secondary sample tube;
    wherein the secondary tube carriages provide lateral access to a secondary tube within the secondary tube carriage from at least two sides of the secondary tube.

2. The system of claim 1, further comprising:
    a sample identification reader for determining sample identification information from a primary sample tube; and
    a host computer, the host computer receiving sample identification information and issuing a sample testing message.

3. The system of claim 2, wherein the sample testing message identifies a number of secondary tubes to receive volumes of a sample.

4. The system of claim 2, wherein the sample testing message identifies a test to be performed by one of the first and the second analyzers.

5. The system of claim 3, wherein the host computer receives the sample identification information output by the sample identification reader.

6. The system of claim 4, wherein the host computer receives the sample identification information output from a first or second analyzer.

7. The system of claim 1, further comprising:
    a first clinical chemistry analyzer coupled to receive secondary tubes from the first secondary tube transfer station;
    a sample identification reader for determining sample identification information from a primary sample tube; and
    a host computer, the host computer receiving sample identification information and issuing a sample testing message.

8. The system of claim 7, further comprising:
    a controller that controls, directly or indirectly, the reading of sample identification information and that controls, directly or indirectly, the first secondary tube transfer station,
    wherein the controller transfers sample identification information to the first clinical chemistry analyzer in conjunction with a transfer of a secondary tube.

9. The system of claim 7, wherein the first clinical chemistry analyzer sends sample identification information to the host computer and receives test instructions from the host computer.

10. The system of claim 1, wherein the storing station receives and stores trays of sample tubes.

11. The system of claim 10, wherein the storing station includes at least one immediate storage tube location and an associated alert mechanism for identifying when an immediate sample is loaded in the system.

12. The system of claim 10, wherein the sampling station comprises a bar code reader for reading a bar code from a label of a primary sample tube and the sample probe comprises a cap piercer for removing liquid from the primary sample tube without removing a cap from the primary sample tube.

13. The system of claim 1, wherein the secondary tube carriages provide lateral access to a secondary tube within the secondary tube carriage from at least two opposite faces of the secondary tube carriage.

14. The system of claim 1, wherein the secondary tube carriages hold a secondary tube in place with resilient clips.

15. The system of claim 1, wherein the secondary tube carriages hold a secondary tube in place using clips that engage an upper and lower portion of a secondary tube.

16. The system of claim 15, wherein the secondary tube carriages provide lateral access to a secondary tube within the secondary tube carriage from at least two opposite faces of the secondary tube carriage.

17. The A clinical chemistry system comprising:
- a sample identification station comprising a sample identification mechanism for determining sample identification information from a primary sample tube;
- a transferring mechanism for transferring a volume of the sample from the primary sample tube into a secondary sample tube;
- a carriage mechanism, comprising a gripper with a pair of opposed arms that close on, grips, and lifts the primary sample tube contained in the holder, whereby the primary sample tube separates from the holder, and transports the primary sample tube to the sample identification station;
- a continuous transport mechanism for moving secondary sample tubes within the system;
- first and second sample tube transfer stations, respectively, for coupling to first and second analyzers, the first and second sample tube transfer stations adapted to move the secondary sample tube from the continuous transport mechanism to an interface of a first or second analyzer; and
- a host computer, the host computer receiving sample identification information and issuing a sample testing message that includes one of the first and second analyzers as a destination;
- wherein the continuous transport mechanism is a continuous belt that travels adjacent the sampling station and the first and second secondary tube transfer station;
- wherein a plurality of sample tube carriages are mounted to the belt, each sample tube carriage adapted for carrying the secondary sample tube;
- wherein the sample tube carriages provide lateral access to the secondary sample tube within the sample tube carriage from at least two sides of the secondary sample tube.

18. The system of claim 17, wherein the destination is determined in accordance with a previous test result transmitted from one of a first and second analyzer to the host computer.

19. The system of claim 17, further comprising:
- a controller that controls the determining of sample identification information and that controls the first sample tube transfer station,
- wherein the controller transfers sample identification information to the first clinical chemistry analyzer in conjunction with a transfer of a secondary tube.

20. The system of claim 19, wherein the first clinical chemistry analyzer sends sample identification information to the host computer and receives test instructions from the host computer.

21. The system of claim 17 farther comprising at least one immediate storage tube location and an associated alert mechanism for identifying when an immediate sample is loaded in the system.

22. The system of claim 17, wherein the sample identification mechanism comprises a bar code reader for reading a bar code from a label of a primary sample tube.

23. The system of claim 17, wherein the sample tube carriages provide lateral access to the secondary sample tube within the sample tube carriage from at least two opposite faces of the secondary sample tube carriage.

24. The system of claim 17, wherein the sample tube carriages hold the secondary sample tube in place with resilient clips.

25. The system of claim 17, wherein the sample tube carriages hold the secondary sample tube in place using clips that engage an upper and lower portion of a sample tube.

26. The system of claim 25, wherein the sample tube carriages provide lateral access to the secondary sample tube within the sample tube carriage from at least two opposite faces of the sample tube carriage.

27. The clinical chemistry system of claim 17, wherein the sample identification mechanism further comprises:
- an identification information reading device for reading sample identification information from the primary tube; and
- a tube spinner for holding and spinning the primary sample tube, whereby the sample identification information can be accessed and determined by the identification information reading device.

28. The clinical chemistry system of claim 27, wherein the sample identification information reading device is a bar code reader.

* * * * *